(12) United States Patent
Weilandt et al.

(10) Patent No.: US 7,041,065 B2
(45) Date of Patent: May 9, 2006

(54) MULTIPLE-USE BIOPSY APPARATUS AND CORRESPONDING SINGLE-USE BIOPSY INSTRUMENT

(76) Inventors: Anders Weilandt, Anhaltsvägen 33, S-191 40 Sollentuna (SE); Mikael Lindgren, Centralvägen 6A, S-194-76 Upplands Väsby (SE); Joakim Jemseby, Mörbylund 11, 5 tr., S-182 30 Danderyd (SE)

( * ) Notice: Subject to any disclaimer, the term of this patent is extended or adjusted under 35 U.S.C. 154(b) by 330 days.

(21) Appl. No.: 10/311,103

(22) PCT Filed: Jun. 14, 2001

(86) PCT No.: PCT/SE01/01361

§ 371 (c)(1),
(2), (4) Date: Feb. 24, 2003

(87) PCT Pub. No.: WO01/95808

PCT Pub. Date: Dec. 20, 2001

(65) Prior Publication Data

US 2003/0163152 A1 Aug. 28, 2003

(30) Foreign Application Priority Data

Jun. 16, 2003 (SE) .................................... 0002281

(51) Int. Cl.
*A61B 10/00* (2006.01)
(52) U.S. Cl. ....................... 600/567; 606/167
(58) Field of Classification Search ........ 600/564–567; 606/167, 170
See application file for complete search history.

(56) References Cited

U.S. PATENT DOCUMENTS

| 4,776,346 | A |   | 10/1988 | Beraha et al. ............... 128/754 |
| 5,025,797 | A |   | 6/1991 | Baran |
| 5,121,751 | A | * | 6/1992 | Panalletta .................... 600/567 |
| 5,125,413 | A |   | 6/1992 | Baran |
| 5,243,994 | A |   | 9/1993 | Ranalletta .................... 128/754 |
| 5,284,156 | A | * | 2/1994 | Schramm et al. ........... 600/567 |
| 5,306,260 | A | * | 4/1994 | Kanner ........................ 600/567 |
| 5,400,798 | A |   | 3/1995 | Baran |
| 5,476,101 | A | * | 12/1995 | Schramm et al. ........... 600/567 |
| 5,507,298 | A | * | 4/1996 | Schramm et al. ........... 600/567 |
| 5,546,957 | A | * | 8/1996 | Heske ......................... 600/567 |
| 5,617,874 | A |   | 4/1997 | Baran |
| 5,655,542 | A |   | 8/1997 | Weilandt .................... 128/754 |
| 6,110,129 | A | * | 8/2000 | Terwilliger ................. 600/567 |
| 6,126,617 | A | * | 10/2000 | Weilandt et al. ............ 600/567 |

FOREIGN PATENT DOCUMENTS

| EP | 0536888 | 4/1993 |
| WO | WO 99/44505 | 9/1999 |

* cited by examiner

*Primary Examiner*—Charles Marmor
*Assistant Examiner*—Michael Apanius
(74) *Attorney, Agent, or Firm*—Patzik, Frank & Samotny Ltd.

(57) ABSTRACT

A single-use biopsy instrument for mounting at a multiple-use biopsy apparatus, comprises a cartridge enclosing proximal end portions of a canula, a finger tube slidingly disposed on the canula, and a stylet slidingly disposed in the canula. The canula and the finger tube have proximal holding portions and are displaceable in regard of the cartridge by displacement means disposed in the biopsy apparatus engaging with the holding portions through one or several engagement openings in one wall of the cartridge. Also disclosed is a corresponding biopsy apparatus.

20 Claims, 19 Drawing Sheets

MULTIPLE-USE BIOPSY APPARATUS AND CORRESPONDING SINGLE-USE BIOPSY INSTRUMENT

FIELD OF THE INVENTION

The present invention relates to a multiple-use biopsy apparatus. The present invention also relates to a single-use biopsy instrument for use with the biopsy apparatus of the invention.

BACKGROUND OF THE INVENTION

The invention departs from an apparatus for collecting tissue samples by excising a segment from tissue, and a corresponding method for harvesting of tissue samples described in WO 99/44505 which is incorporated by reference into this specification. The biopsy apparatus of WO 99/44505 comprises a biopsy instrument and a holder.

In this specification, the terms "proximal" and "distal" refer to the person extracting a biopsy sample; the terms "front" and "rear" have a corresponding meaning. Thus, the proximal end of a biopsy apparatus is its rear end, pointing away from the patient.

The biopsy instrument of WO 99/44505 comprises a canula with a distal open cutting end and a through opening in its wall near the distal end, a finger tube slidingly disposed on the canula and provided with a finger at its distal end, and a stylet slidingly disposed in the canula, the finger being insertable into the opening in the canula wall and axially displaceable in a forward direction so as to be deflected towards the axis of the canula.

The holder of WO 99/44505 comprises a housing, means for releasably coupling the biopsy instrument to the housing; and compressed coil means for consecutive axial displacement of the canula and the tube in combination in a distal direction, and then of the tube in respect of the canula in the same direction. To expel a harvested biopsy sample from the canula, the holder further comprises means for consecutive displacement of the tube, and of the tube and the canula in combination, in a proximal direction. At their respective distal ends of the canula, the tube and the stylet are provided with end sections for mounting in the holder.

WO 99/44504 also discloses a loading assembly for the holder. The loading assembly comprises a loading arm swivellingly attached at its one end to the housing, an intermediate arm swivellingly attached at its one end to the loading arm and at its other end to a catch holding the canula end section during tensioning and in a tensioned position in respect of a tension spring or during compression or in a compressed position in respect of a compressing spring (the latter being preferred), the catch being displaceable in a proximal direction against the resistance of the spring and being adapted to be held there for intentional release.

A biopsy apparatus comprising the holder and the loading assembly of WO 99/44504 can be manufactured for single use in which case it is supplied to the customer preferably with the biopsy instrument of WO 99/44505 already mounted. It can, however, also be designed for repeated use with disposable sets of the biopsy instrument.

The aforementioned biopsy apparatus intended for single use, that is, provided to the user with the biopsy instrument already mounted, does not require other manual skills than performing its proper medical operation, that is, taking a biopsy sample from a patient and expelling the sample from the canula thereafter.

This is not so with the multiple-use biopsy apparatus in which a new biopsy instrument has to be mounted for each biopsy. Since the biopsy apparatus comprises three parts which are slidingly displaceable in regard to each other, their mounting, in a given spatial relationship, requires skillful handling. To this adds the sharp tip of the stylet and the front edge of the canula which may cause wounds if not properly handled in mounting or which may be accidentally damaged, as may be the tiny tissue excision means, that is the finger of the finger tube. Thus there is ample room for improvement in respect of making the loading process a routine measure, including modification of the biopsy apparatus and the loading assembly.

OBJECTS OF THE INVENTION

It is an object of the invention to provide a biopsy apparatus comprising a loading assembly for multiple use in which a disposable biopsy instrument can be easily and safely mounted and dismounted.

It is an object of the invention to provide a corresponding biopsy instrument.

Additional objects of the invention will become obvious from the following short description of the invention, the accompanying drawings illustrating a preferred embodiment of the invention described in greater detail, and the appended claims.

SUMMARY OF THE INVENTION

These and other objects of the invention are achieved by a single-use biopsy instrument of the aforementioned kind designed for mounting in a multiple-use biopsy apparatus. The biopsy instrument includes a cartridge enclosing proximal end portions of the canula, the finger tube, and the stylet. The cartridge is provided with a displaceable lock on one of its sides. The displacement is substantially in the lock plane and in a proximal direction. It is preferred for the cartridge to comprise a safety latch which must be removed before the lock can be displaced. By removing the safety latch and displacing the lock in a proximal direction the biopsy instrument is prepared for mounting at the biopsy apparatus of the invention.

In particular the single-use biopsy instrument for mounting at a multiple-use biopsy apparatus includes a cartridge enclosing proximal end portions of a canula, a finger tube slidingly disposed on the canula, and a stylet slidingly disposed in the canula, the canula and the finger tube having proximal holding portions and being displaceable in regard of the cartridge by displacement means disposed in the biopsy apparatus engaging with said holding portions through one or several engagement openings in one wall of the cartridge.

It is preferred for the cartridge to comprise a cartridge body having an opening on one of its sides covered by a lock in which said one or several engagement openings are disposed. The displacement opening is advantageously a slit extending in parallel with the canula.

According to a first preferred aspect of the invention, the cartridge lock extends outside the cartridge body opening and is displaceable in the lock plane in the direction of the cartridge body so as to cover the opening of the cartridge body opening more fully. It is advantageous for the cartridge lock to be securable in a displaced position at the cartridge body or at an element secured thereat.

According to a second preferred aspect of the invention, the biopsy instrument comprises a removable safety latch partly covering the cartridge body opening. It is particularly preferred for the cartridge lock to be displaceable only upon removal of a safety latch covering a portion of the cartridge body opening.

According to a third preferred aspect of the invention, the holding portion of the stylet is fixed to the cartridge body.

According to a fourth preferred aspect of the invention, the cartridge body comprises laterally disposed projections for mounting in hooks of the biopsy apparatus.

According to the present invention is also disclosed a biopsy apparatus comprising a casing, means for releasably coupling the biopsy instrument of the invention to the casing, compressed coil means disposed in the casing for consecutive axial displacement of the canula and the finger tube in combination in a distal direction, and of the tube in respect of the canula in the same direction, the displacement being effected via a first displacement member slidingly disposed in the casing cooperating with a proximal end portion of the canula of and a second displacement member slidingly disposed in the casing distally of the first displacement member cooperating with a proximal end portion of the finger tube.

According to a fifth preferred aspect of the invention, the first and second displacement members comprise pins extending through a longitudinal slit in the cartridge lock which are engageable with corresponding bores in the end portions of the canula and the finger tube.

According to a sixth preferred aspect of the invention, the biopsy apparatus comprises a mechanism for step-less control of the canula stroke.

According to a seventh preferred aspect of the invention, the biopsy apparatus is designed to receive the entire biopsy instrument cartridge in an opening disposed on one of its sides so as to make the visible side of the cartridge (the cartridge bottom) flush with portions of the same side of the biopsy instrument. It is important for the biopsy instrument cartridge to be relaseably securable in said opening. Preferably the biopsy instrument is securable by means of an axially displaceable frame comprising hooks disposed in the opening, the hooks being releaseably engageable with laterally disposed projections of the cartridge body.

According to an eight preferred aspect of the invention, the biopsy apparatus is provided with a loading mechanism for compression of a spring coil affecting said first and second displacement members, the mechanism comprising a loading arm, a loading catch and an intermediate arm swivellingly fixed at the loading arm and the loading catch. It is preferred for the apparatus to comprise means for releasing the first and second displacement members in combination to displace them in a distal direction by the action of the spring coil. Also preferred is for the apparatus to comprise a stroke limiter for limiting the displacement of the second and/or the first displacement member in a distal direction. Preferably the displacement of the second displacement member is so limited as to make it displaceable further in a distal direction than the first displacement member.

According to still another preferred aspect of the invention, the biopsy apparatus comprises means for expulsion of a harvested biopsy sample from the canula.

By definition, the top side of the biopsy instrument of the invention is the side covered by a lock. The top side of the biopsy apparatus of the invention is the side provided with the loading mechanism. The biopsy instrument is mounted at the bottom side of biopsy apparatus with its top side facing the apparatus.

The invention will now be described by reference to preferred embodiments of the biopsy instrument of the invention and the biopsy apparatus of the invention, by the study of which further advantages of the present invention will become obvious. The preferred embodiments are illustrated in drawings showing rough perspective views thereof.

DESCRIPTION OF PREFERRED EMBODIMENTS

Indications of lateral direction such as 'from above', 'underside', 'top side' are defined by the views of the Figures. The steel coil compression springs are only shown schematically as cylinders.

Figure 4:
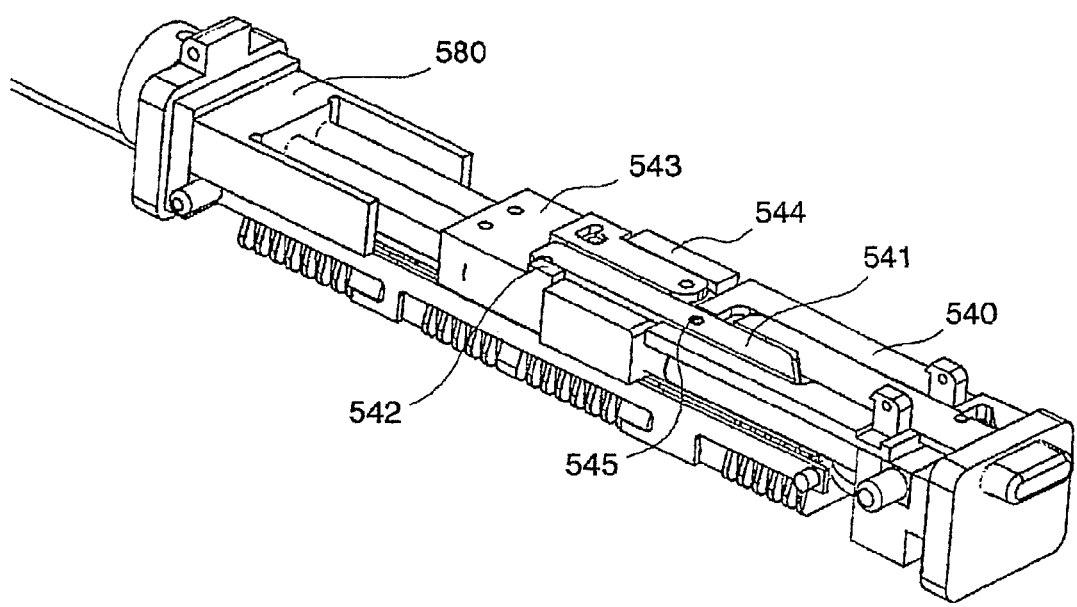
FIG. 4 the biopsy apparatus of FIG. 2 and in the same view, with the casing and part of the loading mechanism removed, in a secured loaded condition.
Figure 16:
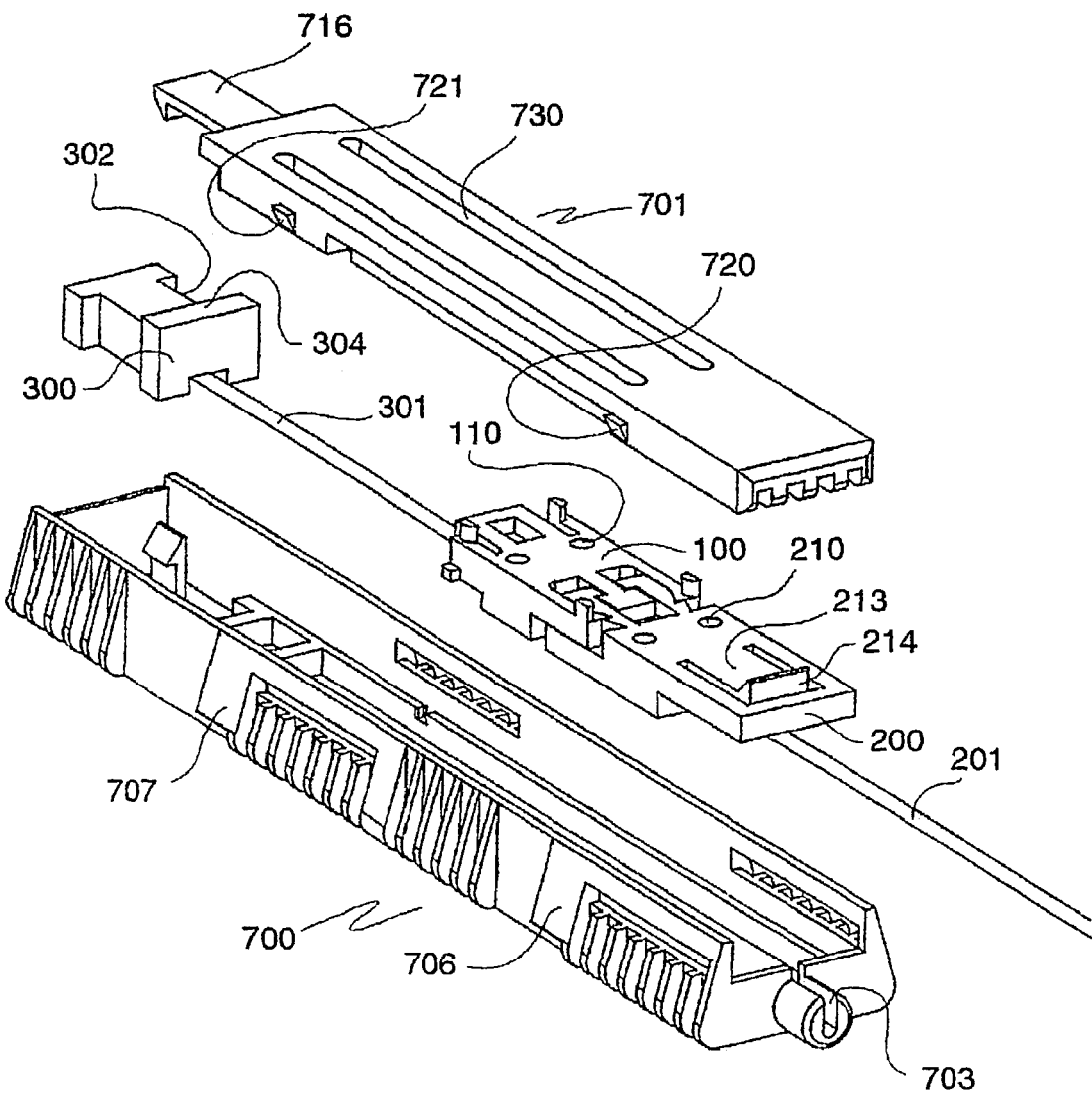
FIG. 16 the biopsy instrument of FIG. 1, in an exploded top/proximal view, without the safety latch.

The biopsy instrument illustrated in FIGS. 1 and 13–19 comprises a canula, a finger tube 201 and stylet 301 of the same kind as illustrated in FIG. 4 of WO 99/44505; see also U.S. Pat. No. 5,644,542, where the design and function of these elements is explained in detail and which is incorporated herein by reference. In FIG. 16 rear (proximal) end portions of the finger tube 201 enclosing the canula and the stylet 301 are shown to illustrate their relationship with their respective holders 200, 300, each made in one piece of a polymer material, preferably an ABS polymer (acrylonitrile-butadiene-styrene copolymer) or another polymer of high impact and tensile strength. Also shown in FIG. 16 is the canula holder 100.

Figure 17:
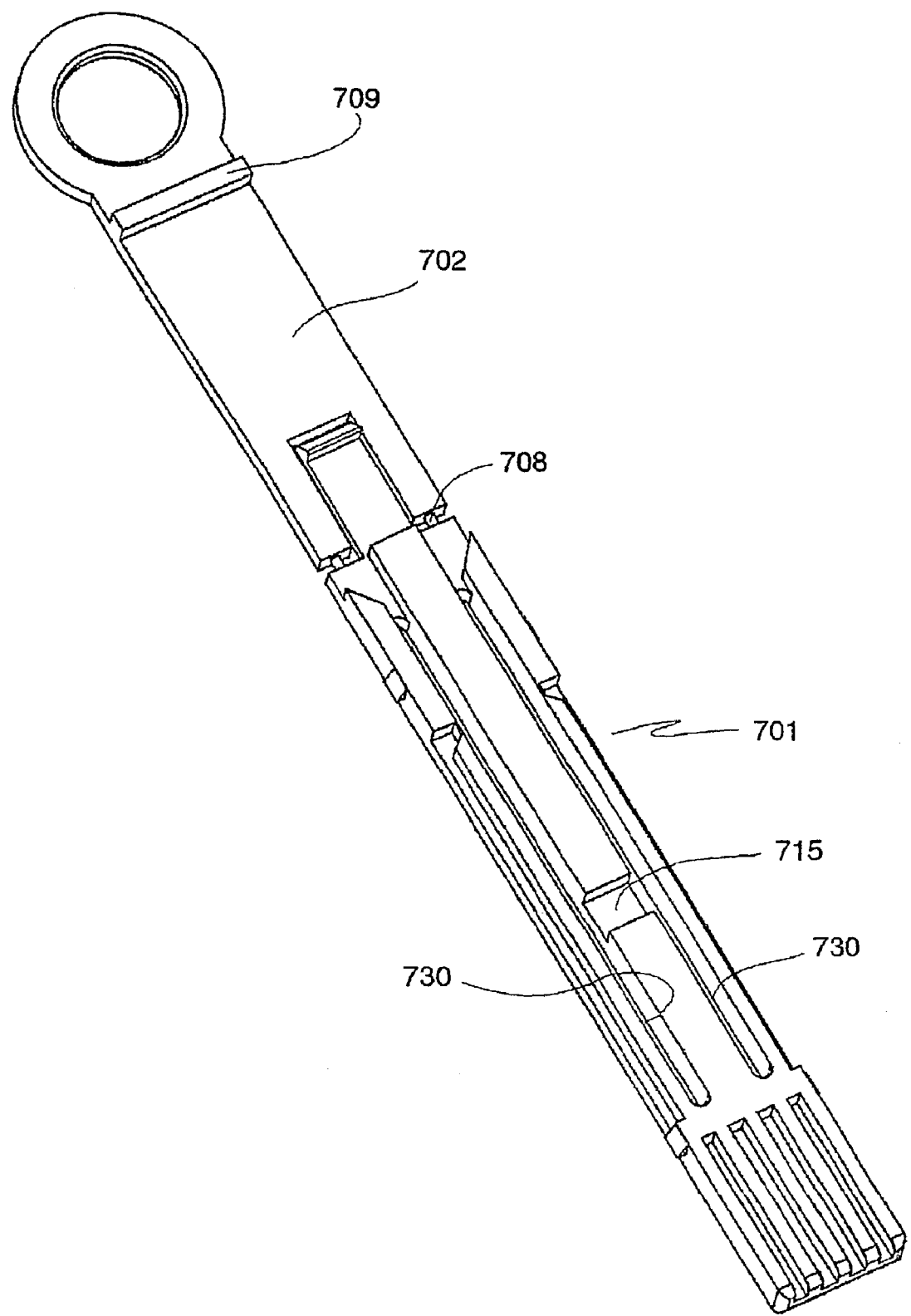
FIG. 17 the cartridge lock and safety latch of the biopsy instrument in FIG. 1, in a bottom/proximal perspective view, aligned but slightly separated.
Figure 18:
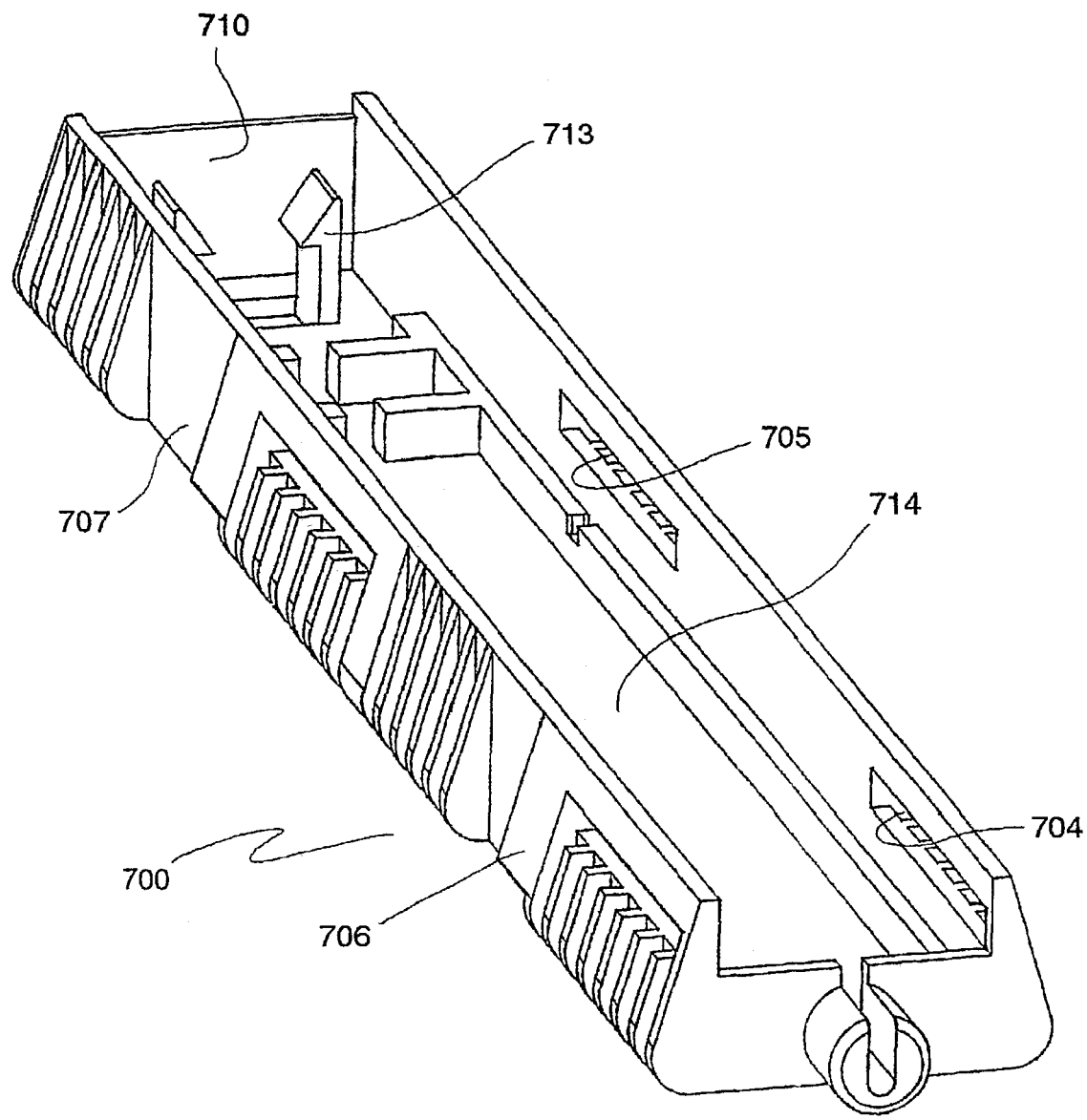
FIG. 18 the cartridge body of the biopsy instrument in FIG. 1, in a front/proximal view.
Figure 19:
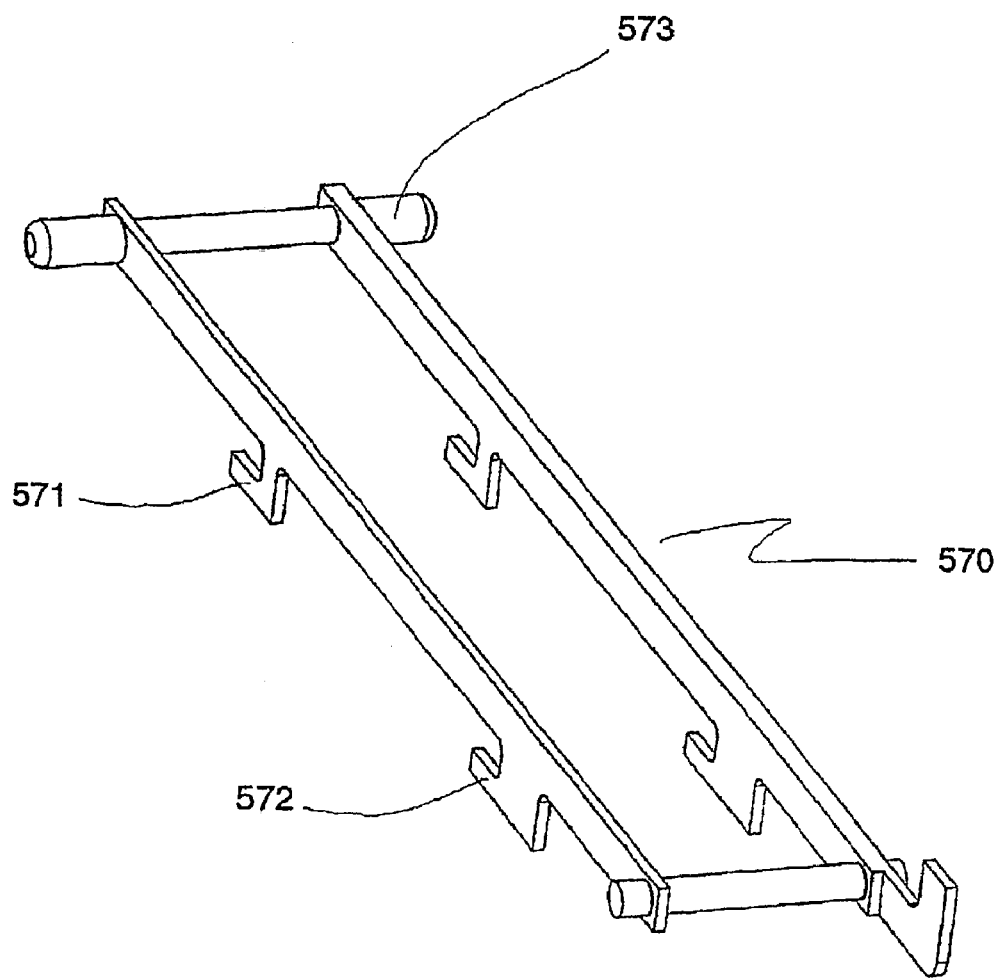
FIG. 19 the cartridge mounting frame, in a top/proximal view.

The canula, the finger tube 201 and the stylet 301 are mounted in a cartridge body 700, a distal portion of which is covered by a lock 701 and a portion adjoining thereto proximally by a safety latch 702 (FIG. 17). The cartridge lock 701 extends over the distal end of the cartridge body 700 and is held by projectures 706, 707 in lateral slits 704, 705 of the latter so that it can be displaced in a distal direction upon removal of the safety latch 702 to cover most of the cartridge body 700. Initially, the safety latch 702 is positionally stabilized in respect of the cartridge lock by pegs 708 extending from its distal end wall inserted in corresponding bores in the proximal end wall of the cartridge lock 701 and a transversal flange 709 at its bottom side abutting the rear wall 710 of the cartridge body 700. It is in this configuration the biopsy instrument of the invention is supplied to the user for mounting at the biopsy apparatus of the invention by a procedure explained further down. The canula, the stylet 301 and the finger tube 201 are mounted in the cartridge body 700 in an assembled state, that is with the canula inserted in the finger tube 201 and the stylet 301 in the canula. The canula, the stylet and the finger tube extend through a slit 703 in the front wall of the cartridge body 700 in a distal direction. The neck 302 of the stylet holder 300 which has an I-profile is snapped between two snaps tongues 713 extending from the bottom 714 of the cartridge body 700. The stylet 301 thus is rigidly secured at the cartridge body 700. In contrast, the canula and finger tube 201 are not definitely fixed but only constrained in their movement inside the cartridge. The distal wall of a lateral notch 715 inside of the cartridge lock 701 cooperates with the tip 214 of a tongue 213 of the finger tube holder 200 projecting above its top face. Thereby the finger tube holder 200 and canula holder 100 proximally abutting thereto can be displaced in a proximal direction by pushing the qartridge lock 701 fully over the cartridge body 700, once the safety latch 702 has been removed by pulling it rearwards while lifting it slightly so as to disengage its transversal flange 709 from the rear wall 710 of the cartridge body. The cartridge lock 701 is pushed back until a snap tongue 716 extending from its proximal end wall engages with an elevated transverse portion 304 of the stylet holder 300. This makes the biopsy instrument ready for mounting at the biopsy apparatus.

Figure 3:
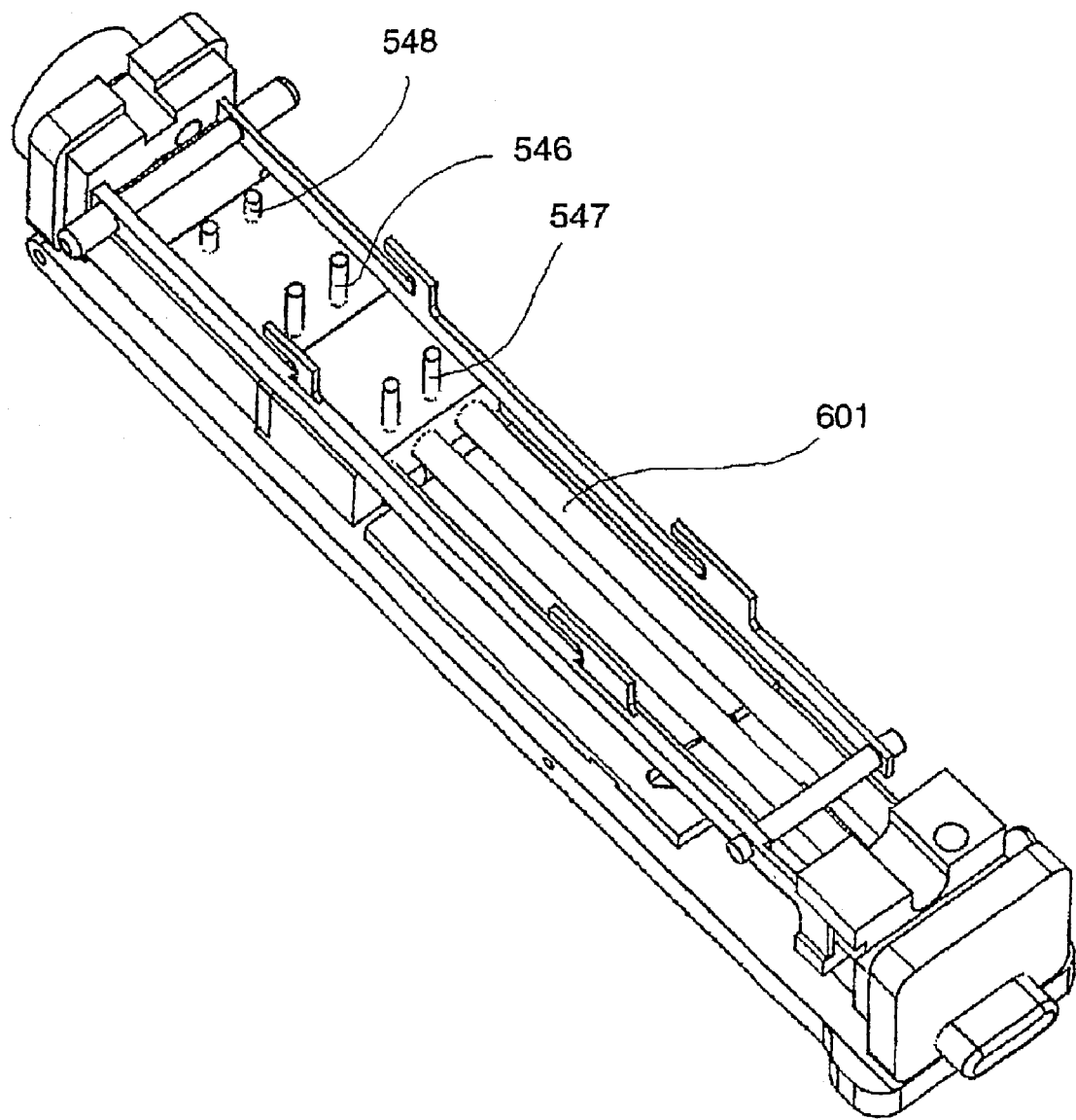
FIG. 3 the biopsy apparatus of FIG. 1, in a distal side/bottom view, with the biopsy instrument removed.

The biopsy apparatus of the invention comprises a casing 500 consisting of two substantially symmetrical halves sectioned perpendicular to the larger faces of the holders 100, 200. The casing 500 which has about the form of a rectangular bar can be of a suitable polymer, for instance polycarbonate, but preferably of metal, such as aluminum or stainless steel, since the biopsy apparatus has to withstand rough cleaning and sterilizing conditions. The casing halves fit by appropriate design of rims and other elements, such as snaps (not shown) but may also be connected by bolts or similar means. The casing includes a loading assembly according to WO 99/44505 to which reference is made and by which holders 100, 200 are brought to a 'loaded' position from which they can be released for tissue sampling. Instead of the single spring coil of the apparatus of WO 99/44505 three spring coils 601 disposed in parallel are provided; for simplicity reason they are only shown as cylinders in the drawings (FIG. 3).

Figure 1:
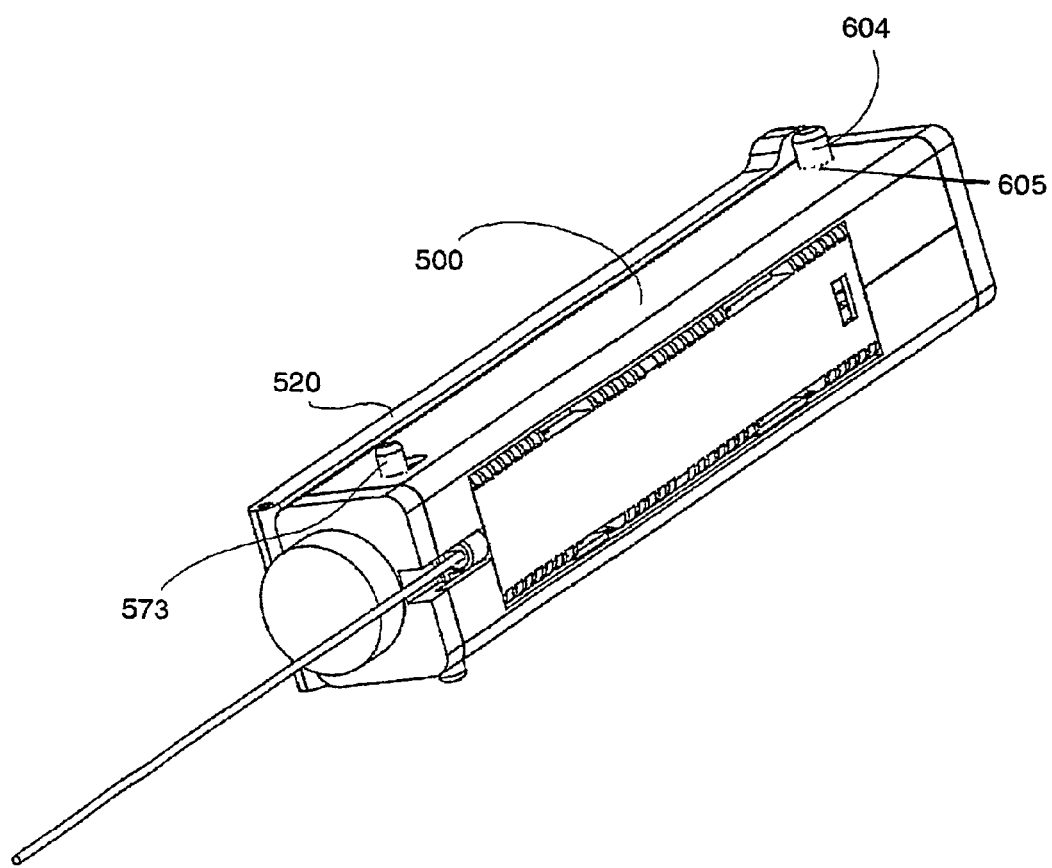
FIG. 1 a preferred embodiment of the biopsy apparatus of the invention, with a biopsy instrument mounted, in a proximal side/bottom view, with the loading arm abutting the casing.
Figure 2:
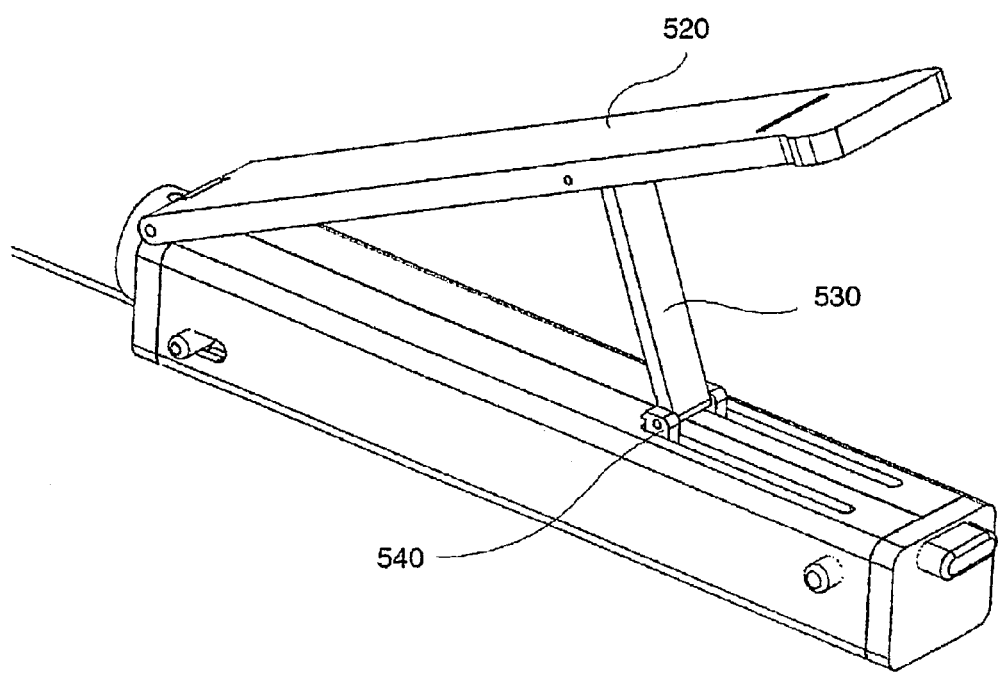
FIG. 2 the biopsy apparatus of FIG. 1 in a distal side/top view, with the loading arm raised.
Figure 11:
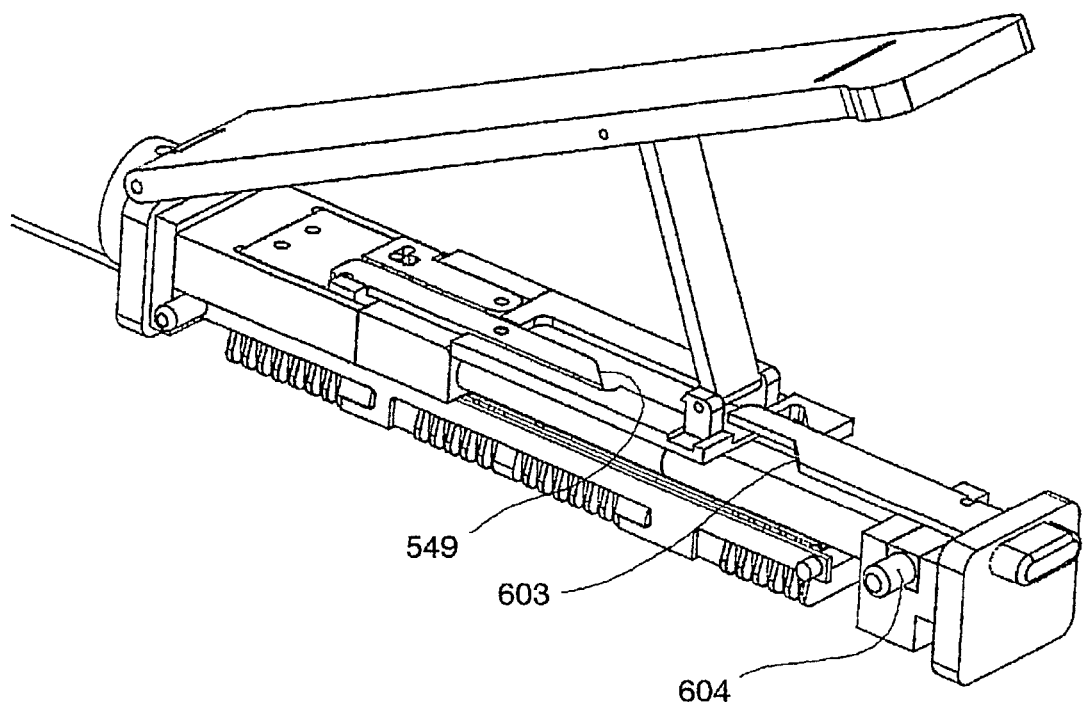
FIG. 11 the biopsy apparatus of FIG. 5 but with the loading arm shown, in the same view, at the start of a loading operation.
Figure 12:
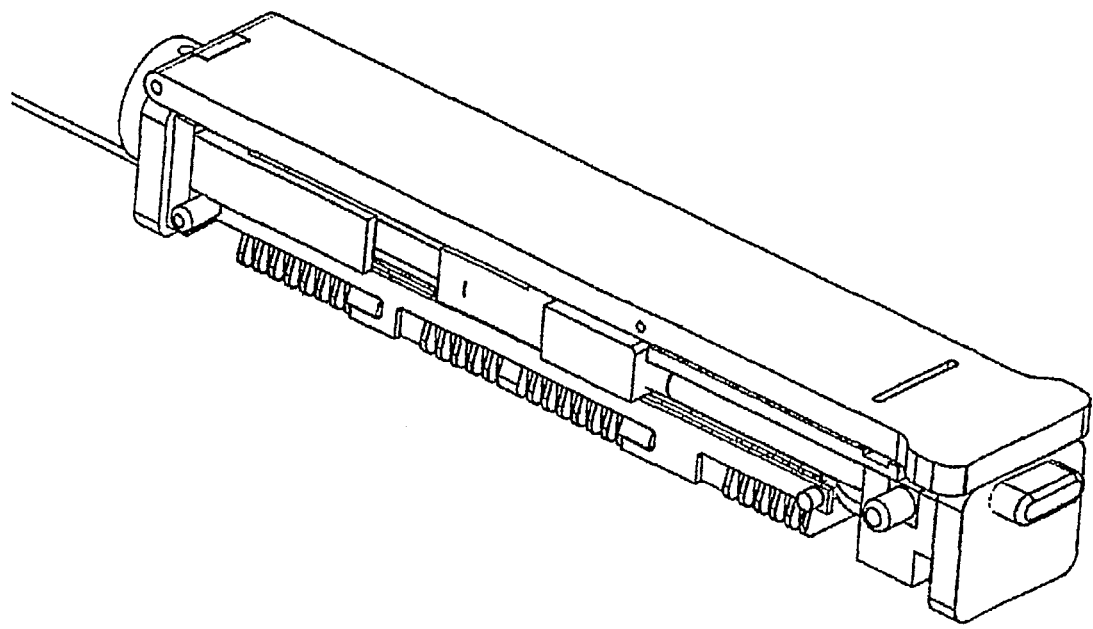
FIG. 12 the biopsy apparatus of FIGS. 11, at the end of a loading operation.
Figure 13:
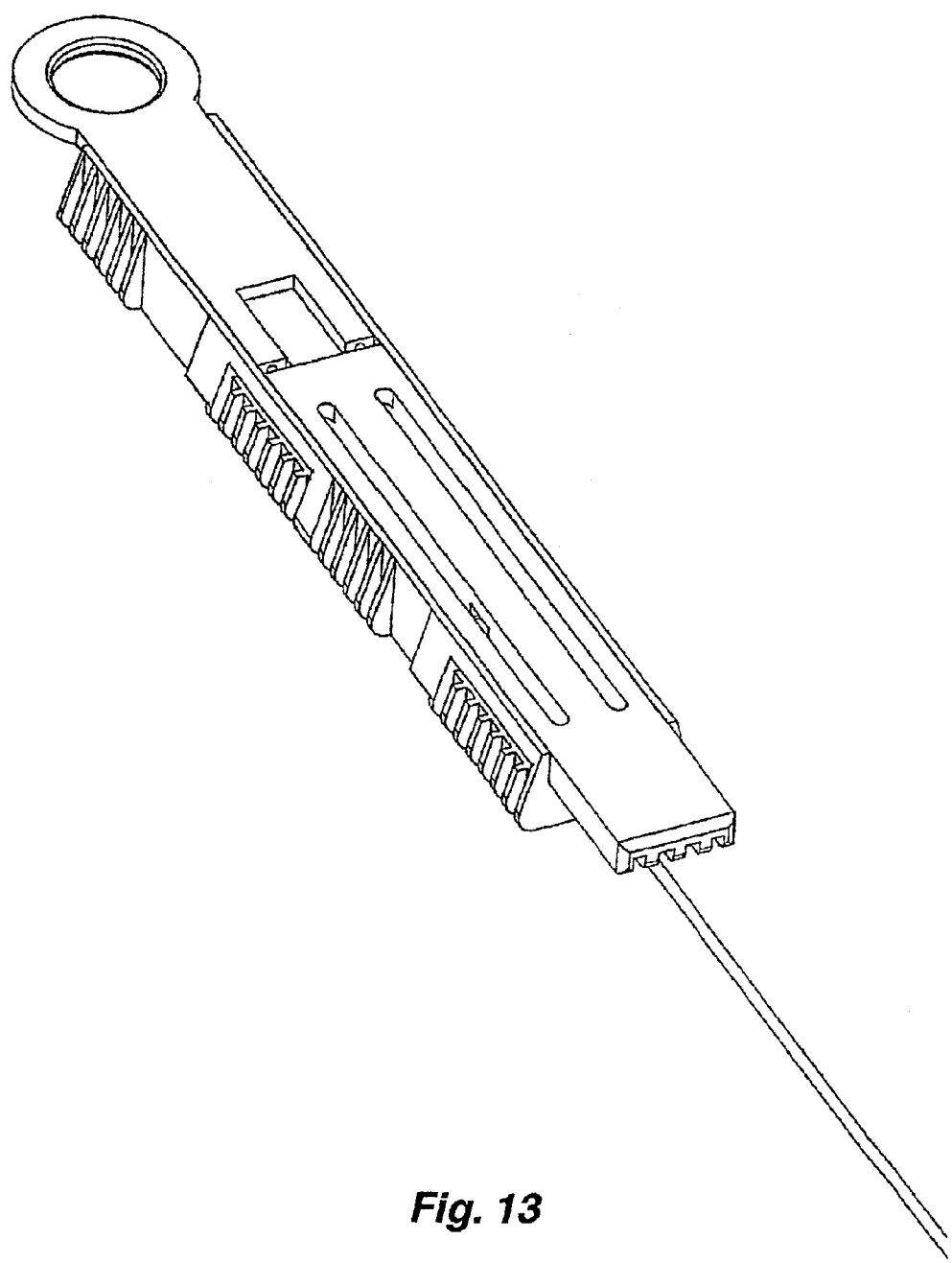
FIG. 13 the biopsy instrument of FIG. 1, in a top/proximal view, complete with the safety latch.
Figure 14:
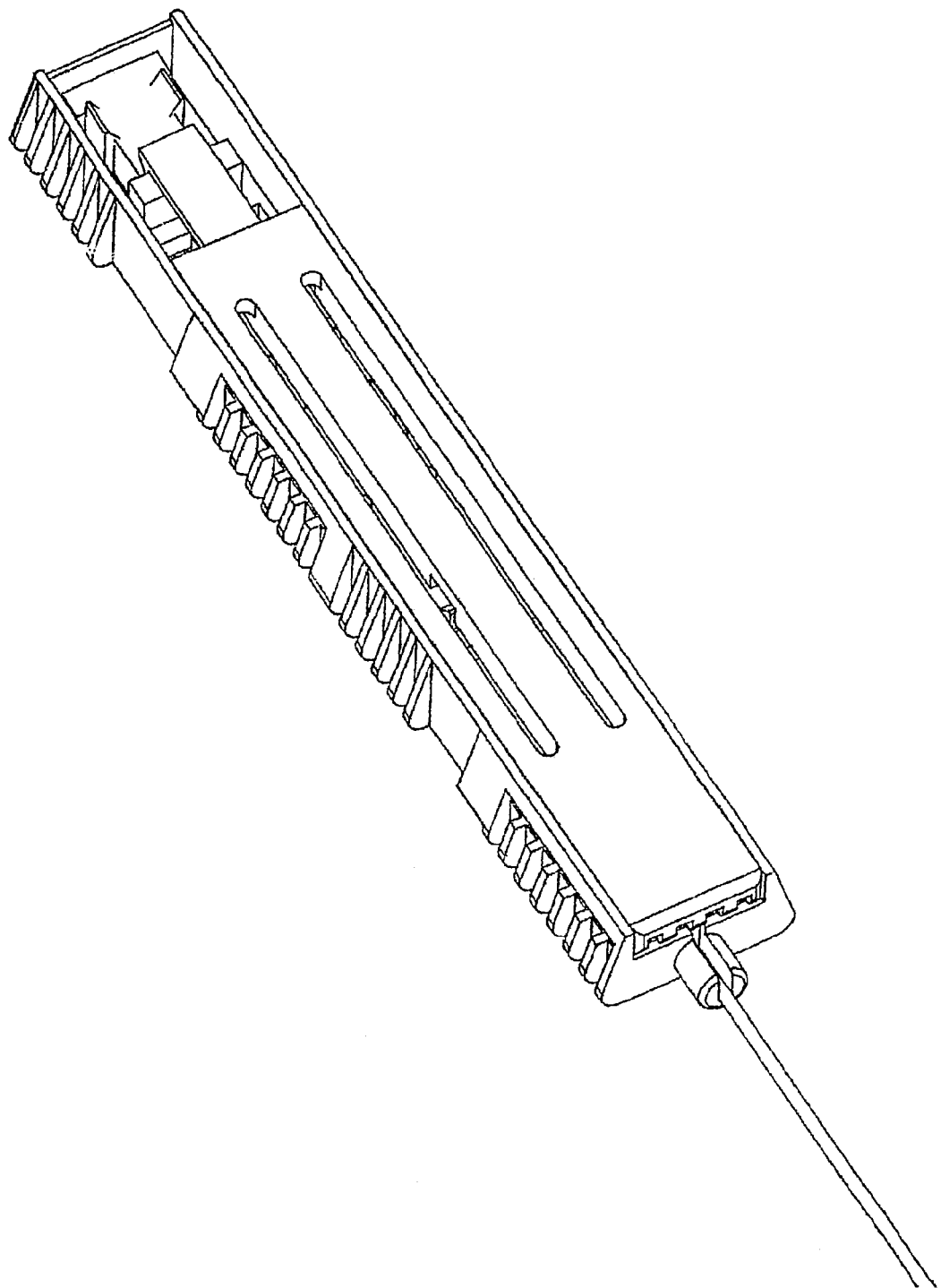
FIG. 14 the biopsy instrument of FIG. 1, in another top/proximal view, with the safety latch removed and the cartridge lock inserted.
Figure 15:
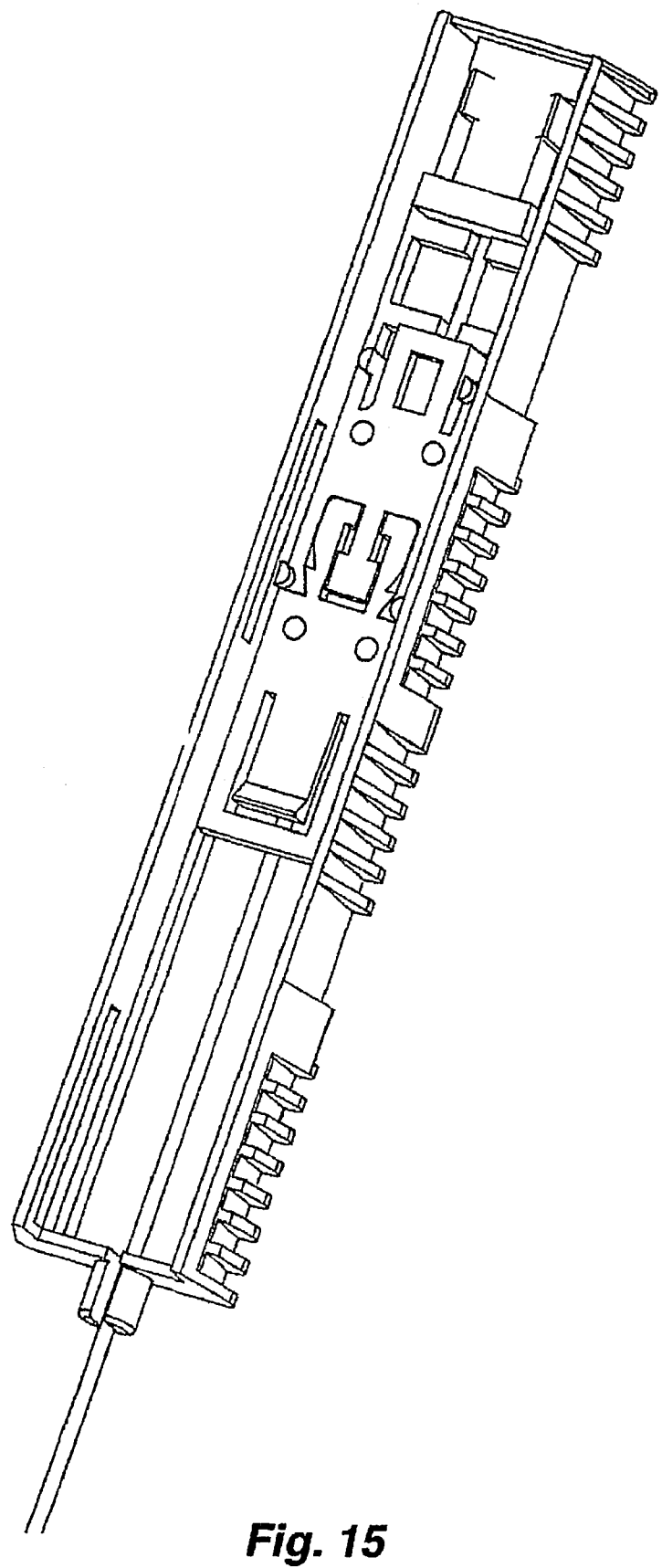
FIG. 15 the biopsy instrument of FIG. 1, in still another top/proximal view, with the cartridge lock removed.

In contrast to the arrangement in WO 99/44505 in which the holders 100, 200 of the biopsy instrument are directly displaced against the force of a spring coil in the loading procedure, the present invention employs intermediate structures pertaining to the biopsy apparatus termed finger tube and canula control members 543,544 (FIG. 4) which provide for control of the biopsy instrument by the biopsy apparatus. The finger tube and canula control members having coupling pins disposed at their lower faces for engagement with the finger tube holder and the canula holder, respectively. The finger tube control member 543 has one pair of coupling pins 546 (FIG. 3), the canula control member 544 also has one pair 547 (FIG. 3). In addition the finger tube control member has a pair of guide pins 548 disposed distally of the finger tube coupling pins 546 which guide pins 548 are shorter than the coupling pins. Thus two longitudinally extending parallel rows of coupling and guide pins result. The coupling pins of each pin row are arranged to engaged with corresponding bores disposed in the finger tube holder bores 210, and the canula holder, bores 110. The control members 543,544 with their guide and coupling pins are accessible from outside through an opening in the bottom wall of the casing 500. The opening is of a size allowing the cartridge to be fully inserted and secured in the inserted position by an axially displaceable mounting frame 570 (FIG. 19) comprising pairs of hooks 571,572 which engage with rectangular front and rear shoulders 720,721 extending laterally from the cartridge body 700. The mounting frame 570 can be operated from outside by knobs 573 extending through openings in the lateral walls of the casing 500. The engagement of the pairs of coupling pins 546, 547 of the control members 543,544 with the pairs of bores 210,110 in the finger tube holder 200 and the canula holder 100, respectively, is provided for by two longitudinally extending slits 730 in the cartridge lock 701. To provide for easy loading the loading assembly (FIG. 2) employs three elements, a loading arm 520 an intermediate arm 530, and a loading catch 540 comprising a catch arm 541 (FIG. 4) holding the finger tube control member 543 during compression of the spring coils 601 and in their compressed (loaded) state. With its hook-like front end of the catch arm 541 the catch 540 grips a loading grip 542 of the finger tube control member 543. The canula control member 544 is in turn held in position by the finger tube control member 543. The canula holder/finger tube holder assembly 100, 200 can be released from the loaded state by an oblong trigger 600 disposed distally/laterally of the catch 540. The rear end of trigger 600 forming a release button 602 passes through an opening in the rear wall of the casing 500. By pressing the release button 602 the trigger 600 is pushed forwards whereby a slanting portion 603 (FIG. 11) of it affects a slanting rear face 549 of the catch arm 541 which is journalled at 545, so to make it swivel by a few degrees, thereby releasing the grip 542 and, hence, the finger tube control member 543 and the finger tube holder 200. The biopsy apparatus can be secured in the loaded position by a transversely displaceable locker pin 604 disposed near the rear end of the housing in through bores 605 of the casing. In a secured position the locker pin 604 cooperates with an arc-formed cutout of the trigger 600.

Figure 5:
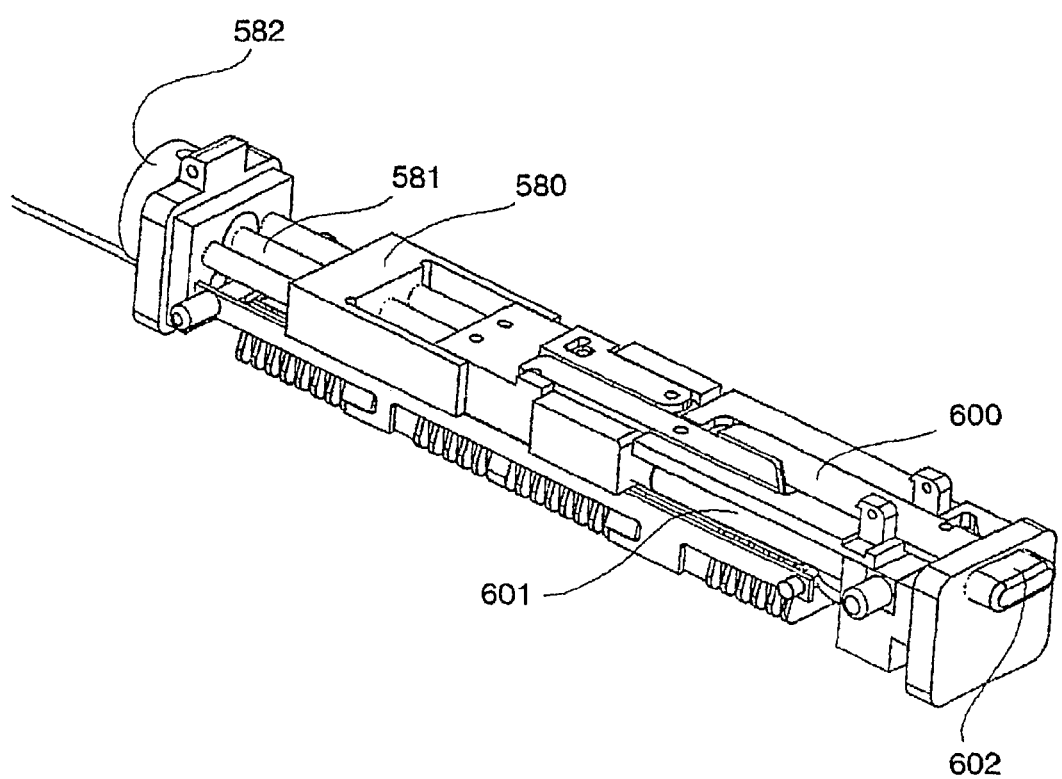
FIG. 5 the biopsy apparatus of FIG. 4 and in the same view and condition, with a shorter stroke length set.
Figure 6:
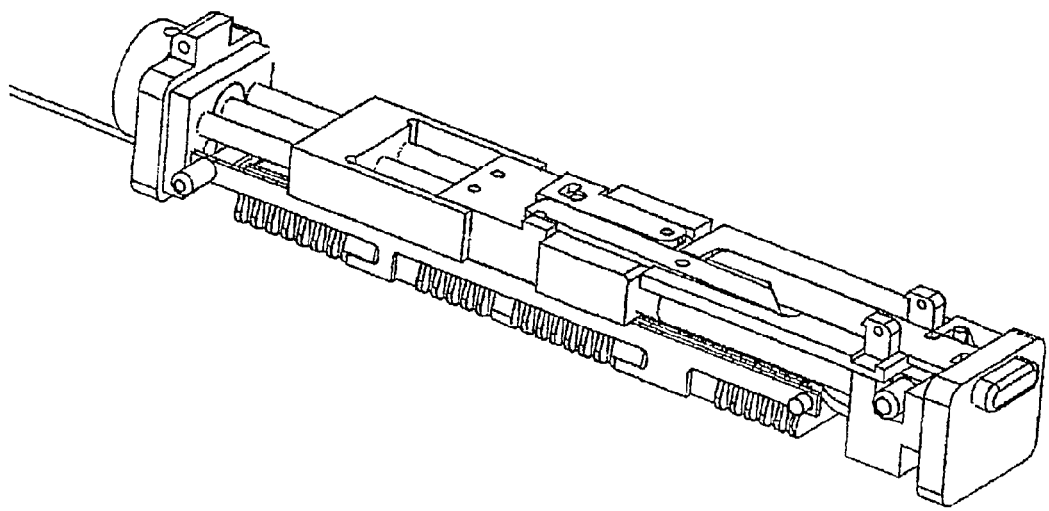
FIG. 6 the biopsy apparatus of FIG. 5, in the same view, in an unsecured loaded condition.
Figure 7:
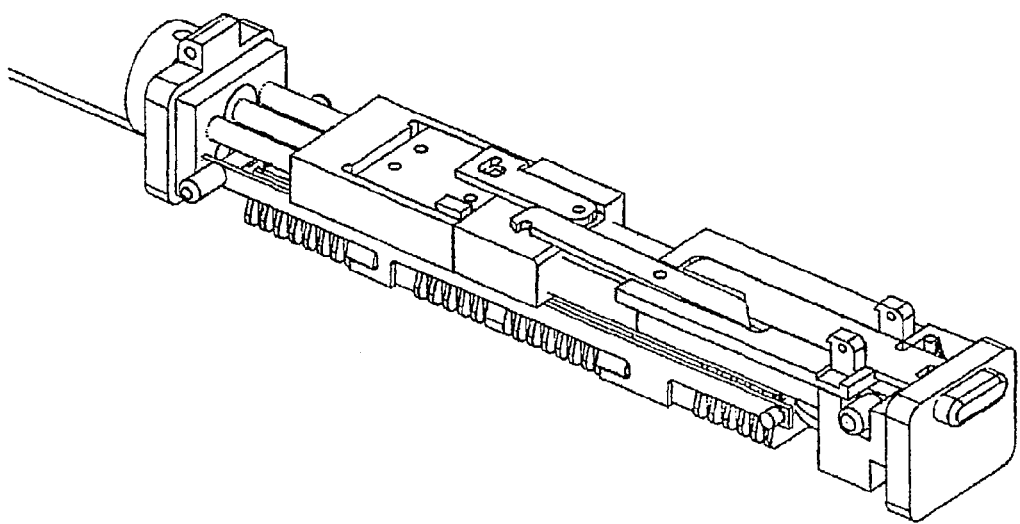
FIG. 7 the biopsy apparatus of FIG. 5, in the same view, in a released condition at the end of the canula movement.
Figure 8:
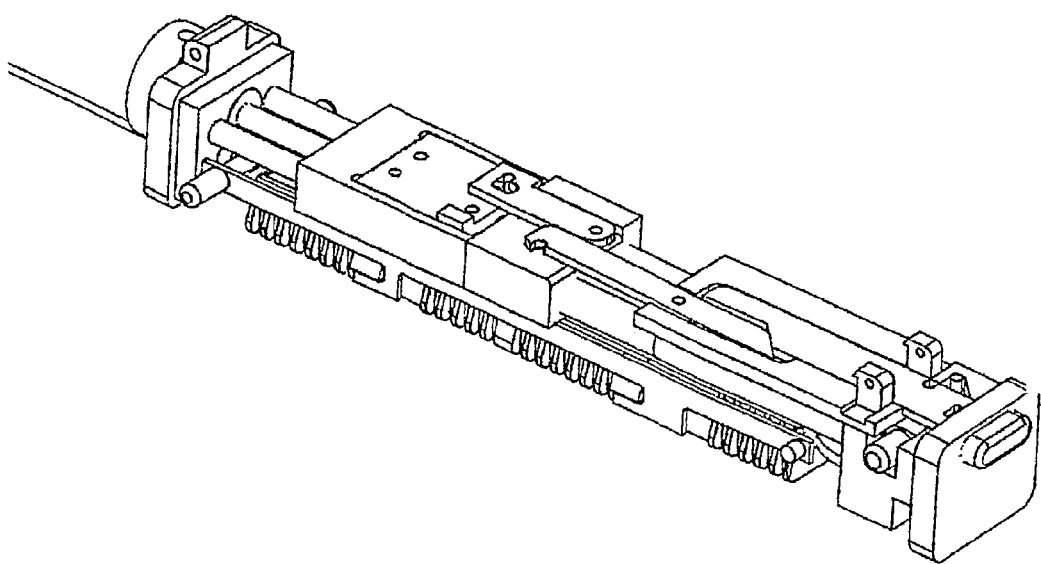
FIG. 8 the biopsy apparatus of FIG. 5, in the same view, in a released condition at the end of the finger tube movement.
Figure 9:
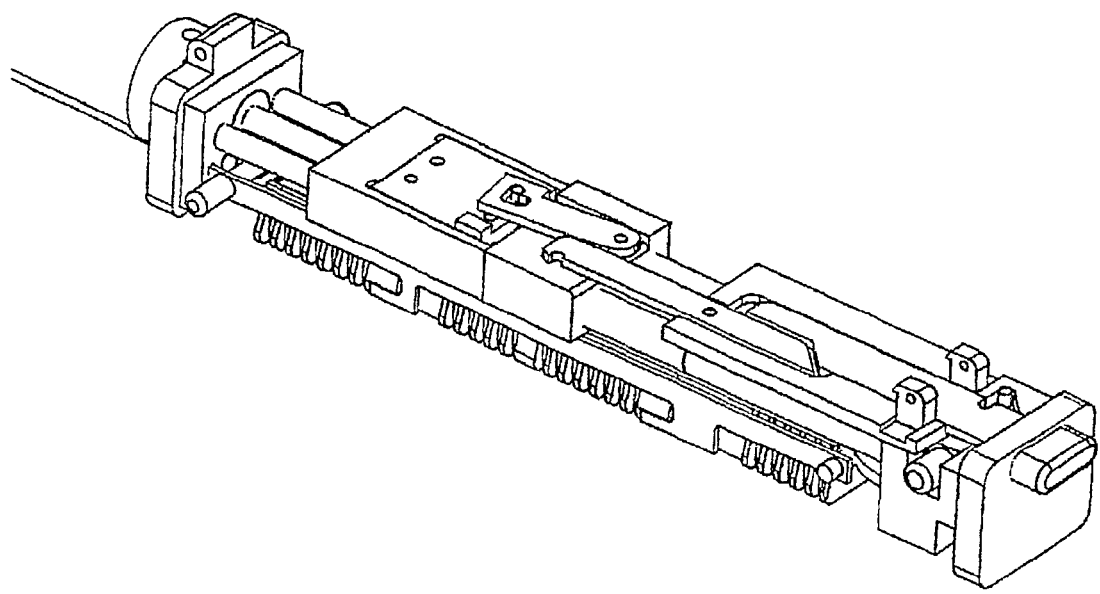
FIG. 9 the biopsy apparatus of FIG. 5, in the same view, after withdrawal of the finger from the canula but before sample expulsion and loading.
Figure 10:
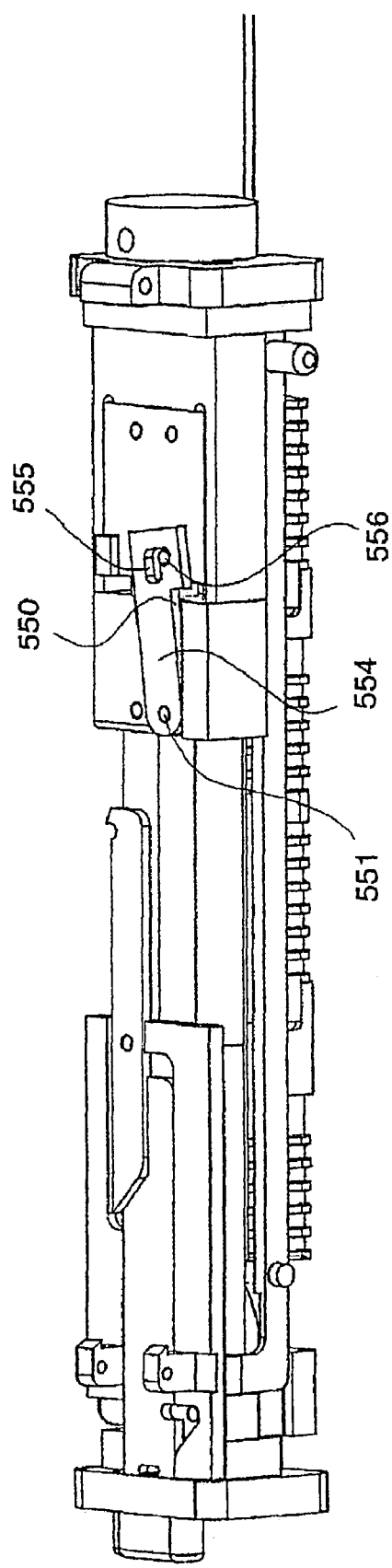
FIG. 10 the biopsy apparatus of FIG. 5, in a frontal top view, after sample expulsion.

A biopsy sampling cycle will now by explained by reference to FIGS. 4–10. In FIG. 4 the biopsy instrument is in a loaded and secured position. In FIG. 5 the stroke length has been reduced from the maximally possible by displacing the stroke limiter 580 in a distal direction by means of a screw mechanism of which the screw 581 and the knob 582 disposed at the front face of the biopsy apparatus for continuous setting the stroke length is shown, whereas an additional release mechanism by which any stroke setting can be released to provide for maximum stroke length setting is not shown. Next (FIG. 6), the locker pin 604 is unsecured (the stylet 301 will have been injected into the tissue at this stage but this is not shown) and the trigger 600 is pushed forwards by pressing the release buttom 602. The figure shows the situation just after the front end of the catch arm has released the loading grip 542 of the finger tube control member 543. In FIG. 7 the situation at the end of the first phase of biopsy sampling is shown, that is when the combined distal movement of the canula and the finger tube 201 along the stylet 301 has come to an end whereby the distal movement of the canula is stopped by the front face of the canula control member 544 hitting the side bar end faces of the U-formed stroke limiter 580. FIG. 8 illustrates the situation at the end of the second phase of biopsy sampling, that is when the distal movement of the finger tube 201 is stopped by the base of the U-formed stroke limiter 580. In FIG. 9 the person taking a biopsy sample has ceased the thumb pressure on the release button 602. This allows the catch arm 541 to swivel back to its original position, thereby permitting a spring-loaded (at 550) L-formed lever 554 to swing by a few degrees around a pinion 551 by which it is fixed at upper face of the finger tube control member 543. At its frontal transversal section the L-formed lever 554 has an L-shaped through opening 555 with the same orientation as the lever 554. A pin 556 extending from the upper face of the canula control member 544 extends into the opening 555 in which it had been disposed up to now along the vertical L-bar of the opening 555. By the slight rotation of the lever the pin 556 is now located at the free end of the transversal L-bar of the opening 555 while the finger tube control member 543 has been slightly withdrawn from the canula control member which is sufficient for withdrawing the finger tip of the finger tube 201 from the opening in the canula wall. This, in combination with the release (not shown) of the stroke limiter 580 to allow it to move back to the maximum stroke position, provides for the ejection of the biopsy sample from the canula in the next step, the situation at the end of which is illustrated in FIG. 10. Thereafter the biopsy apparatus is again loaded and the used biopsy instrument released from the apparatus by displacing the mounting frame 570 in a distal direction by means of knobs 571.

The invention claimed is:

1. A single-use biopsy instrument for mounting at a multiple-use biopsy apparatus, the biopsy instrument comprising a cartridge enclosing proximal end portions of each of a canula, a finger tube slidingly disposed on the canula, and a stylet slidingly disposed in the canula, the canula and the finger tube having proximal holding portions, the cartridge including a cartridge body with an opening in one wall with a lock covering the opening and with engagement openings formed in the lock, and displacement elements disposed in the biopsy apparatus engaging with the holding portions through at least one of the engagement openings in for enabling displacement of the canula and the finger tube with respect to the cartridge.

2. The biopsy instrument of claim 1, wherein each engagement opening is a slit extending parallel to the canula.

3. The biopsy instrument of claim 1, wherein the cartridge lock extends outside the cartridge body opening and is displaceable in a plane of the lock in the direction of the cartridge body.

4. The biopsy instrument of claim 3, wherein the cartridge lock is securable at the cartridge body or an in a displaced position.

5. The biopsy instrument of claim 3, wherein the cartridge lock is non-displaceable, until a safety latch covering a portion of the cartridge body opening and associated with the lock removed.

6. The biopsy instrument of claim 1, comprising a removable safety latch partly covering the cartridge body opening.

7. The biopsy instrument of claim 1, wherein a holding portion of the stylet is fixed to the cartridge body.

8. The biopsy instrument of claim 1, wherein the cartridge body comprises laterally disposed projections, mounting in hooks of the biopsy apparatus engageable on the projections.

9. A biopsy apparatus comprising the biopsy instrument of claim 1, a casing, means for releasably coupling the biopsy instrument to the casing, at least one compressed coil disposed in the casing for consecutive axial displacement of the canula and the finger tube in combination in a distal direction, and of the tube in respect of the canula in the same direction, a first displacement member slidingly disposed in the casing and cooperating with a proximal end portion of the canula, and a second displacement member slidingly disposed in the casing distally of the first displacement member and cooperating with a proximal end portion of the finger tube, wherein the first and second displacement members cause the axial displacement.

10. The biopsy apparatus of claim 9, wherein the first and second displacement members comprise pins extending through the engagement openings in the cartridge lock and engageable with corresponding bores in the end portions of the canula and the finger tube.

11. The biopsy apparatus of claim 10, further comprising a releasing device for releasing the first and second displacement members in combination to enable displacement of the displacement members in a distal direction by the action of the at least one compressed coil.

12. The biopsy apparatus of claim 11, further comprising a stroke limiter for limiting the displacement of the second displacement member in a distal direction.

13. The biopsy apparatus of claim 11, further comprising a stroke limiter for limiting the displacement of the first displacement member in a distal direction.

14. The biopsy apparatus of claim 13, wherein the stroke limiter so limits the displacement of the second displacement member as to make the second displacement member displaceable further in a distal direction than the first displacement member.

15. The biopsy apparatus of claim 9, comprising a mechanism for continuous setting of the canula stroke length.

16. The biopsy apparatus of claim 9, further comprising an opening on one side of the casing and shaped to receive the entire biopsy instrument cartridge.

17. The biopsy apparatus of claim 16, wherein the biopsy instrument cartridge is releasably securable in the casing opening.

18. The biopsy apparatus of claim 17, further comprising an axially displaceable frame comprising hooks disposed in the opening of the casing, the hooks being releaseably engageable with laterally disposed projections of the cartridge body for securing the biopsy instrument.

19. The biopsy apparatus of claim 9, further comprising a loading mechanism for compression of the at least one coil, the at least one coil comprises a spring coil affecting the first and second displacement members, the loading mechanism comprising a loading arm, a loading catch and an intermediate arm swivellingly fixed at the loading arm and the loading catch.

20. The biopsy apparatus of claim 9, further comprising a device for expelling a harvested biopsy sample from the canula.

* * * * *